United States Patent
Chen et al.

(10) Patent No.: US 10,314,923 B2
(45) Date of Patent: Jun. 11, 2019

(54) SILYBIN INJECTION AND PREPARATION METHOD THEREFOR

(71) Applicant: TASLY PHARMACEUTICAL GROUP CO., LTD., Tianjin (CN)

(72) Inventors: Jianming Chen, Tianjin (CN); Baoan Gao, Tianjin (CN); Qinqin Zhou, Tianjin (CN); Shuiping Zhou, Tianjin (CN); Nan Cai, Tianjin (CN); Yuansheng Zhang, Tianjin (CN); Chan Wu, Tianjin (CN); Nong Yu, Tianjin (CN); Lina Chen, Tianjin (CN); Wenli Liu, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 0 days.

(21) Appl. No.: 15/541,556

(22) PCT Filed: Dec. 24, 2015

(86) PCT No.: PCT/CN2015/098713
§ 371 (c)(1),
(2) Date: Jul. 5, 2017

(87) PCT Pub. No.: WO2016/110193
PCT Pub. Date: Jul. 14, 2016

(65) Prior Publication Data
US 2018/0000965 A1 Jan. 4, 2018

(30) Foreign Application Priority Data
Jan. 5, 2015 (CN) .......................... 201510001635

(51) Int. Cl.
| | | |
|---|---|---|
| *A61K 9/00* | (2006.01) | |
| *A61K 9/08* | (2006.01) | |
| *A61K 9/16* | (2006.01) | |
| *A61K 9/19* | (2006.01) | |
| *A61K 41/00* | (2006.01) | |
| *A61K 47/02* | (2006.01) | |
| *A61K 47/10* | (2017.01) | |
| *A61K 47/12* | (2006.01) | |
| *A61K 47/24* | (2006.01) | |
| *A61K 47/26* | (2006.01) | |
| *A61K 47/69* | (2017.01) | |
| *A61K 31/357* | (2006.01) | |

(52) U.S. Cl.
CPC ........ *A61K 47/6951* (2017.08); *A61K 9/0019* (2013.01); *A61K 9/08* (2013.01); *A61K 9/1682* (2013.01); *A61K 9/19* (2013.01); *A61K 31/357* (2013.01); *A61K 41/0009* (2013.01); *A61K 47/02* (2013.01); *A61K 47/10* (2013.01); *A61K 47/12* (2013.01); *A61K 47/24* (2013.01); *A61K 47/26* (2013.01)

(58) Field of Classification Search
None
See application file for complete search history.

(56) References Cited

FOREIGN PATENT DOCUMENTS

| | | |
|---|---|---|
| BY | 17987 C1 | 2/2014 |
| CN | 1391894 A | 1/2003 |
| CN | 1593591 A | 3/2005 |
| CN | 1679542 A | 10/2005 |
| CN | 1961874 A | 5/2007 |
| CN | 101130088 A | 2/2008 |
| CN | 101966196 A | 2/2011 |
| CN | 102960500 A | 3/2013 |
| CN | 103372169 A | 10/2013 |
| CN | 103655929 A | 3/2014 |
| CN | 103751798 A | 4/2014 |
| CN | 103830204 A | 6/2014 |
| EP | 0209037 A1 | 1/1987 |
| RU | 2314797 C2 | 1/2008 |
| RU | 2318538 C1 | 3/2008 |

OTHER PUBLICATIONS

CN1391894A, published Jan. 22, 2003, machine translation.*
Kwon, Bull. Korean Chem. Soc. 2010, vol. 31, No. 10, 3035.*
CN1762345, published Apr. 26, 2006, machine translation.*
Pramanick, Pharma Times—vol. 45, No. 3, Mar. 2013.*
Yuecheng et al.; "Research Progress in Pharmacologic Effect of Silymarin"; Chinese Journal of Hospital Pharmacy; Aug. 2001; 21(8); p. 493-494.
Hongchen et al. "Research on Dissolving of Silybin"; Beijing Medical College; Chinese Pharmaceutical Bulletin; 1983; 19(12); 8 pages.
Wu et al.; "Analysis of silibinin in rat plasma and bile for hepatobiliary excretion and oral bioavailability application"; Journal of Pharm. Biomedical Analysis.; 2007; 45(4); p. 635-641.
Filburn et al.; "Bioavailability of silybin-phosphatidylcholine complex in dogs"; J. Vet. Pharmacol Ther.; 2007; 30(2); p. 132-138.
"Silybin-Phosphatidylcholine Complex"; Alternative Medicine Review; Thorne Research, Inc.; 2009; 14(4); p. 385-390.
Yun-Mei et al.; "Preparation of Silybin Nanoemulsion and Pharmacokinetics in Rabbits"; Journal of China Pharmaceutical University; 2005; 36(5); p. 427-431 (contains abstract).
International Patent Application No. PCT/CN2015/098713; Int'l Written Opinion and Search Report; dated Mar. 4, 2016; 7 pages.
Koo et al.; "Effects of Camellia sinensis Extracts on the Antioxidant System and Alcohol Down-Regulation Enzymes in Sub-Acute Ethanol Treated ICR Mice"; Journal of the Korean Society of Food Science and Nutrition; vol. 36 No. 9; 2007; p. 1134-1139 (English Abstract).
Grattagliano et al.; "A silybin-phospholipids complex counteracts rat fatty liver degeneration and mitochondrial oxidative changes"; World Journal of Gastroenterology; vol. 19 No. 20; May 2013; p. 3007-3017.

(Continued)

*Primary Examiner* — Layla D Berry
(74) *Attorney, Agent, or Firm* — BakerHostetler LLP

(57) ABSTRACT

A silybin injection contains silybin, sulfobutyl ether-β-cyclodextrin, an organic solvent for injection, a pH regulator, and may further contain a co-solvent, a lyophilization bulking agent, and water for injection.

19 Claims, 3 Drawing Sheets

(56) References Cited

OTHER PUBLICATIONS

Abascal et al.; "Kudzu—the Miracle Vine"; Alternative & Complementary Therapies; Apr. 2007; p. 78-85.

Falasca et al.; "Treatment with Silybin-Vitamin E-Phospholipid Complex in Patients with Hepatitis C Infection"; Journal of Medical Virology; vol. 80; 2008; p. 1900-1906.

Matteucci et al.; "Liver Disease in Diabetes Mellitus: Potential Therapeutic Value of Vitamin E-Silybin Phytosomal Complex"; Immunology, Endocrine and Metabolic Agents in Medicinal Chem; vol. 10 No. 2; 2010; p. 84-90.

Liu et al.; "Clinical Effect of Silymarin Combined with Levocarnitine on Nonalcoholic Fatty Liver Disease"; China Modern Medicine; vol. 16 No. 7; Apr. 2009; p. 19-20 (abstract).

\* cited by examiner

SILYBIN INJECTION AND PREPARATION METHOD THEREFOR

CROSS-REFERENCE TO RELATED APPLICATIONS

This application is the National Stage of International Application No. PCT/CN2015/098713, filed Dec. 24, 2015, which claims the benefit of Chinese application number 201510001635.8, filed Jan. 5, 2015 the disclosures of which are incorporated herein by reference in their entireties.

TECHNICAL FIELD

The present invention relates to the technical field of medicines, and particularly to a silybin injection and a preparation method therefor.

BACKGROUND ART

Silybin is a flavone compound extracted from seed coats of seeds of a compositae medicinal plant, i.e. silybum marianum. The flavone compound is poor in water solubility and lipid solubility. The structural formula is as follows:

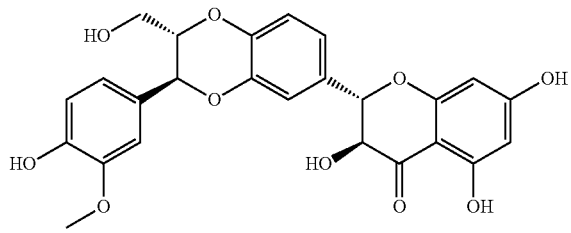 [SMILES: COc1cc([C@@H]2Oc3cc([C@@H]4Oc5cc(O)cc(O)c5C(=O)[C@H]4O)ccc3O[C@H]2CO)ccc1O]

Silybin has an obvious hepatoprotective effect, has different levels of protection and treatment effects on various types of hepatic injury caused by hepatic poisons such as carbon tetrachloride, thioacetamide, hydroxycholine, phalloidine, mucronatine, etc., and has a certain inhibition effect on increasing of alanine aminotransferase caused by carbon tetrachloride. As an ideal hepatic injury repairing medicine, silybin is widely and clinically used for treating hepatopathy such as acute and chronic hepatitis, hepatic fibrosis, early hepatocirrhosis, etc. Due to high medicine effects and low toxicity (Yu Yuecheng, Gu Changhai. Research Progress in Pharmacologic Effect of Silymarin [J]. Chinese Journal of Hospital Pharmacy, 2001, 21(8): 493-494.), silybin has received great attention from discovery.

At present, the preparations sold in China comprise silybin meglumine tablets (approval number: H32026233 approved by the state; manufacturer: Jiangsu Zhongxing Pharmaceutical Co., Ltd.; approval number: H33022182 approved by the state; manufacturer: Zhejiang Donzri Pharmaceutical Co., Ltd.) and silybin capsules (commodity name: Shui Lin Jia; approval number: H20040299 approved by the state; manufacturer: Tianjin Tasly Pharmaceutical Co., Ltd.). The preparations are all oral preparations. The silybin is poor in water solubility and lipid solubility (Wang Hongchen. Research on Dissolving Property of Silymarin [J]. Chinese Pharmaceutical Bulletin, 1983, 19(12): 23-25.), resulting in low oral bioavailability and relatively high first-pass effect. According to report, the absolute bioavailability of silybin taken orally is only 0.95% (Wu J W, et al. Analysis of silybin in rat plasma and bile for hepatobiliary excretion and oral bioavailability application [J]. J Pharm Biomed Anal, 2007, 45(4): 635-641.), and therefore, the exertion of medicine effects of the silybin oral preparations is severely weakened. Thus, people are intended to further exert the medicine effects by improving the bioavailability of silybin. The broad masses of medicinal workers are intended to improve the dissolution of silybin using techniques such as salification, solubilization, solid dispersion, etc. so as to improve the oral absorptivity, but the high effect is not achieved. In addition, Tianjin Tasly Pharmaceutical Co., Ltd. developed a silybin-phosphatidylcholine complex (common name: silybin capsules; commodity name: Shui Lin Jia; approval number: H20040299 approved by the state); and the silybin-phosphatidylcholine complex has been sold in the market. Researches indicate that the dissolution and the bioavailability of the silybin-phosphatidylcholine complex are obviously improved in comparison with those of the common silybin oral preparations and the bioavailability is improved by 3-5 times (Filburn C R, et al. Bioavailability of silybin-phosphatidylcholine complex in dogs [J]. J Vet Pharmccol Ther, 2007, 30(2): 132-138, silybin-phosphatidylcholine complex [M]. Altern Med Rev, ID: Thorne Research, Inc. 2009, 14(4): 385-390.), but the bioavailability is still not ideal. Thus, people consider developing silybin into an injection so as to fundamentally solve the problem of low oral bioavailability.

Song Yunmei et al. (Song Yunmei et al. Preparation of Silybin Nanoemulsion and Pharmacokinetics in Rabbits [J] Journal of China Pharmaceutical University, 2005, 36(5): 427.) developed a silybin nanoemulsion. Since the solubility of silybin is poor, and a large amount of cremophor RH is added into a formulation, the material has severe anaphylaxis and hemolysis, and the safety is poorer. In addition, since silybin is soluble in water under an alkaline condition, researchers developed a silybin N-methylglucamine injection, but silybin is very unstable in an alkaline environment, so that the injection has relatively poor long-term storage stability and is easy to degrade. Therefore, someone prepared a silybin meglumine solution into a freeze-dried powder injection. Although the problem of placement stability of the silybin meglumine solution can be solved, the pH value of the silybin N-methylglucamine aqueous solution is about 11, and thus, the local irritation is high and more adverse effects are generated during injection. According to clinical application of silybin in recent years, it is verified that silybin has precise curative effect and very low toxicity, and the clinical application of silybin is extremely wide. If a safe and injectable silybin preparation can be developed, the bioavailability can be improved, and the pharmacological effect can be fully exerted, so that the medicine effect can be greatly improved, and the great economic and social benefits can be necessarily generated.

A cyclodextrin inclusion compound is formed by wrapping medicine molecules in cavity structures of cyclodextrin molecules, thereby solving the dissolution problem of water-insoluble medicines. However, it is known that the conventional cyclodextrin materials have obvious hemolysis or renal toxicity, such as β-cyclodextrin, hydroxypropyl-β-cyclodextrin, etc. The Chinese patent application CN200410041364.0 with the title "preparation method of cyclodextrin inclusion compound of silybin marianum extract and medicinal preparation thereof" and the publication number of CN159351A has the key technical features of dissolving silybin extract with cyclodextrin using ethanol or isopropanol, performing reduced-pressure evaporation to remove ethanol or isopropanol, and then adding some excipients to prepare an oral preparation or directly sub-packaging to form a sterile powder for injection. The types of cyclodextrin recorded in the Claims and Description are as follows: β-cyclodextrin, hydroxypropyl-β-cyclodextrin, hydroxyethyl-β-cyclodextrin, methyl-β-cyclodextrin, glucosyl-β-cyclodextrin and sulfonyl-β-cyclodextrin. These types of cyclodextrin are conventional cyclodextrin having large toxic and adverse effects, and cannot be truly applied to preparations for intravenous injection, and therefore, the whole embodiment is oriented to the oral preparation and the matching property of the cyclodextrin is not further researched. It is verified through tests that all the types of cyclodextrin defined in this patent cannot be prepared into stable silybin injections (See embodiment 1 of the present invention). The Chinese patent application CN02125823.6 with the title "silymarin injection containing cyclodextrin or derivatives thereof" and the publication number of CN1391894A, according to the implementing scheme recorded in the Description, has the key technical features of adding silymarin into an aqueous solution containing cyclodextrin, regulating the pH of the solution to alkalinity using sodium hydroxide to dissolve silybin, and then regulating the pH value to be 6.0 to 6.5 using hydrochloric acid to obtain a silymarin cyclodextrin inclusion compound, wherein the types of the cyclodextrin are exactly same as that of the patent application (Chinese patent application CN200410041364.0). It is verified through tests that in the process of dissolving silybin in an alkaline aqueous solution of sodium hydroxide, the color of the solution turns dark gradually, and the solution is finally changed into a yellow green solution; through full-wavelength scanning, a greater absorption peak occurs in the part of 326.0 nm again besides the great adsorption occurs in the original part of 287.5 nm, thereby indicating that sodium hydroxide has the effect of obviously breaking the structure of silymarin; and therefore, the quality of the silymarin cyclodextrin inclusion compound prepared by the patent application has a certain problem and may influence the safety and effectiveness. Meanwhile, the freeze-dried powder injection prepared according to the implementing scheme fails to re-dissolve fully after freeze-drying (See embodiment 33 of the present invention). In addition, the types of cyclodextrin recorded in the Claims and Description are conventional cyclodextrin having large toxic and adverse effects, and have potential safety hazard such as hemolysis or renal toxicity.

Sulfobutylether-β-cyclodextrin (SBE-β-CD) is an ionized β-cyclodextrin (β-CD) developed by Cydex Pharmaceuticals, Inc., and has the advantages of good water solubility, no renal toxicity and no hemolysis in comparison with the conventional cyclodextrin materials. Therefore, in combination with the physicochemical properties of silybin, the present invention firstly utilizes sulfobutylether-β-cyclodextrin (SBE-β-CD) to solve the dissolution problem of silybin. Through a great quantity of test researches, a silybin sulfobutylether-β-cyclodextrin inclusion compound is successfully developed and is a safe and stable silybin injection, thereby overcoming the defect of low oral bioavailability of silybin fundamentally, and providing a novel preparation for the clinical research and application.

SUMMARY OF THE INVENTION

An object of the present invention is to provide a safe and stable silybin injection. With respect to the inherent physicochemical properties of silybin and the defects of the preparations in the prior art, a formulation matching same is preferred, so that the silybin injection is successfully developed.

The present invention provides a silybin injection, which is characterized by containing silybin, sulfobutylether-β-cyclodextrin and an organic solvent for injection, wherein the organic solvent for injection is used to dissolve the silybin. The silybin is prepared into a molecular type solution which is then mixed with sulfobutylether-β-cyclodextrin aqueous solution, so that silybin molecules are wrapped in sulfobutylether-β-cyclodextrin molecules, thereby forming a silybin sulfobutylether-β-cyclodextrin inclusion compound. If the formulation constituents do not contain the organic solvent for injection, the silybin inclusion compound cannot be prepared with the conventional method for preparing a cyclodextrin inclusion compound (directly adding medicine powder into a cyclodextrin aqueous solution and stirring until clarity) (see embodiment 2 of the present invention). Therefore, the combination of an organic solvent for injection with sulfobutylether-β-cyclodextrin in the present invention is one of the necessary conditions for preparation of the silybin inclusion compound and also the key feature of the present invention. The silybin injection provided by the present invention may further contains a cosolvent, wherein the cosolvent can, on the one hand further improve the inclusion rate of the silybin, and on the other hand assist in fast and good re-dissolution of freeze-dried samples. The cosolvent enables the silybin injection prepared by the present invention to have more reliable quality. Therefore, the cosolvent is also an important technical feature of the present invention (see embodiment 3 of the present invention).

The present invention provides a silybin injection, which is characterized by being prepared from the following constituents (by weight/volume percentage):

| | |
|---|---|
| silybin | 0.05-1.0% |
| sulfobutylether-β-cyclodextrin | 2-50% |
| organic solvent for injection | 0.5-10% |
| cosolvent | 0-1.0% |
| bulking agent | 0-20% |
| pH regulator | regulating the pH value to be 2.0-8.0 |
| water for injection | as the rest. |

The present invention provides a silybin injection, which is characterized by being prepared from the following constituents (by weight/volume percentage):

| | |
|---|---|
| silybin | 0.1-0.8% |
| sulfobutylether-β-cyclodextrin | 2-30% |
| organic solvent for injection | 0.5-5% |
| cosolvent | 0.001-0.5% |
| bulking agent | 0-15% |
| pH regulator | regulating the pH value to be 2.0-7.0 |
| water for injection | as the rest. |

The present invention provides a silybin injection, which is characterized by being prepared from the following constituents (by weight/volume percentage):

| | |
|---|---|
| silybin | 0.1-0.5% |
| sulfobutylether-β-cyclodextrin | 2-10% |
| organic solvent for injection | 1-5% |
| cosolvent | 0.005-0.5% |
| bulking agent | 3-10% |
| pH regulator | regulating the pH value to be 2.5-6.0 |
| water for injection | as the rest. |

In the silybin injection of the present invention, the percentage contents of various constituents are measured by weight/volume percentage, i.e. the content of solute contained in solution per unit volume, for example, including but not limited to, g/ml, kg/L, etc., which can be enlarged or reduced proportionally with the ratio unchanged.

In the silybin injection, the organic solvent for injection is selected from one or more of polyethylene glycol 200, polyethylene 300, polyethylene glycol 400, polyethylene glycol 600, absolute ethyl alcohol and propylene glycol; and the polyethylene glycol 400 is preferred.

The cosolvent is selected from one or more of distearoyl phosphatidylethanolamine-polyethylene glycol 2000 (DSPE-MPEG2000), distearoyl phosphatidylethanolamine-polyethylene glycol 5000 (DSPE-MPEG5000), polysorbate 80, polyoxyl hydrogenated castor oil, and poly(ethylene glycol)-block-poly(propylene glycol)-block-poly(ethylene glycol); and the distearoyl phosphatidylethanolamine-polyethylene glycol 2000(DSPE-MPEG2000) is preferred.

The bulking agent is selected from one or more of mannitol, lactose, dextran 20, dextran 40, dextran 70, sucrose, xylitol, sorbitol and trehalose; and the mannitol, the lactose and the dextran 40 are preferred.

The pH regulator is selected from one or more of citric acid, hydrochloric acid, glacial acetic acid, phosphoric acid, disodium hydrogen phosphate, sodium dihydrogen phosphate, dipotassium hydrogen phosphate, monopotassium phosphate, disodium citrate, trisodium citrate and sodium acetate; the pH value is regulated to be 2 to 8 and is preferably regulated to be 2 to 7; and then the pH value is preferably regulated to be 2.5 to 6.0.

A silybin injection of the present invention is characterized by being a silybin injection solution.

A silybin injection of the present invention is characterized by being a silybin freeze-dried powder for injection.

A silybin injection of the present invention is in the form of a colorless clear solution or white solid freeze-dried powder for injection.

A preparation method of the silybin solution injection of the present invention is characterized by comprising the following steps of: weighing a prescribed amount of silybin and an organic solvent for injection, containing a cosolvent if necessary, mixing them together, and heating and stirring the mixture at the temperature of 40° C. to 70° C. to make it dissolve, to obtain an organic phase; weighing a prescribed amount of sulfobutylether-β-cyclodextrin and putting same in a suitable amount of water for injection, and stirring the mixture to make it dissolve, to obtain an aqueous phase; mixing the organic phase with the aqueous phase uniformly, and diluting with water for injection to full dose, to obtain a medicine solution; regulating the pH value of the medicine solution to be 2 to 8 using a pH regulator; adding 0.05 w/v %-0.5 w/v % of activated carbon for injection to perform adsorption for 15 to 60 minutes, then filtering the solution through a 1 μm titanium rod to remove carbon, and removing bacteria through a 0.22 μm filter element; performing sub-packaging and sealing to obtain the silybin solution injection.

Preferably, a preparation method of the silybin solution injection of the present invention comprises the following steps of: weighing, a prescribed amount of silybin and an organic solvent for injection, adding a cosolvent if necessary, mixing them together, and heating and stirring the mixture at the temperature of 50° C. to 60° C. to make it dissolve, to obtain an organic phase; weighing a prescribed amount of sulfobutylether-β-cyclodextrin and putting same in a suitable amount of water for injection, and stirring the mixture to make it dissolve, to obtain an aqueous phase; mixing the organic phase with the aqueous phase uniformly, and diluting with water for injection to full dose, to obtain a medicine solution; regulating the pH value of the medicine solution to be 2.5 to 6.0 using a pH regulator; adding 0.1 w/v %-0.3 w/v % of activated carbon for injection to perform adsorption for 30 to 45 minutes, then filtering the solution through a 1 μm titanium rod to remove carbon, and removing bacteria through a 0.22 μm filter element; and performing sub-packaging and sealing to obtain the silybin injection solution.

A preparation method of the silybin freeze-dried powder for injection of the present invention is characterized by comprising the following steps of: weighing a prescribed amount of silybin and an organic solvent for injection, adding a cosolvent if necessary, mixing them together, and heating and stirring the mixture at the temperature of 40° C. to 70° C. to make it dissolve, to obtain an organic phase; weighing a prescribed amount of sulfobutylether-β-cyclodextrin and a bulking agent, putting them in a suitable amount of water for injection, and stirring the mixture to make it dissolve, to obtain an aqueous phase; mixing the organic phase with the aqueous phase uniformly, and diluting with water for injection to full dose, to obtain a medicine solution; regulating the pH value of the medicine solution to be 2 to 8 using a pH regulator; adding 0.05 w/v %-0.5 w/v % of activated carbon for injection to perform adsorption for 15 to 60 minutes, then filtering the solution through a 1 μm titanium rod to remove carbon, and removing bacteria through a 0.22 μm filter element; and performing sub-packaging, freeze-drying and sealing to obtain the silybin freeze-dried powder for injection.

Preferably, a preparation method of the silybin freeze-dried powder for injection of the present invention comprises the following steps of: weighing a prescribed amount of silybin and an organic solvent for injection, adding a cosolvent if necessary, mixing them together, and heating and stirring the mixture at the temperature of 50° C. to 60° C. to make it dissolve, to obtain an organic phase; weighing a prescribed amount of sulfobutylether-β-cyclodextrin and a bulking agent, putting them in a suitable amount of water for injection, and stirring the mixture to make it dissolve, to obtain an aqueous phase; mixing the organic phase with the aqueous phase uniformly, and diluting with water for injection to full dose, to obtain a medicine solution; regulating the pH value of the medicine solution to be 2.5 to 6.0 using a pH regulator; adding 0.1 w/v %-0.3 w/v % of activated carbon for injection to perform adsorption for 30 to 45 minutes, then filtering the solution through a 1 μm titanium rod to remove carbon and removing bacteria through a 0.22 μm filter element; performing sub-packaging, freeze-drying and sealing to obtain a silybin freeze-dried powder for injection.

A silybin injection of the present invention is characterized in that in combination with the inherent physicochemical properties of silybin, the formulation constituents and dosage matching same are preferred, so that the silybin injection is successfully developed. The silybin injection has the characteristics of safety, stability and high medicine-loading capacity, and fundamentally overcomes the defect of low bioavailability of the existing silybin oral preparations, thereby hopefully further exerting the pharmacological effects of silybin to the maximum extent, and laying a foundation for the clinical application and research of silybin.

DETAILED DESCRIPTION OF THE INVENTION

Figure 1:
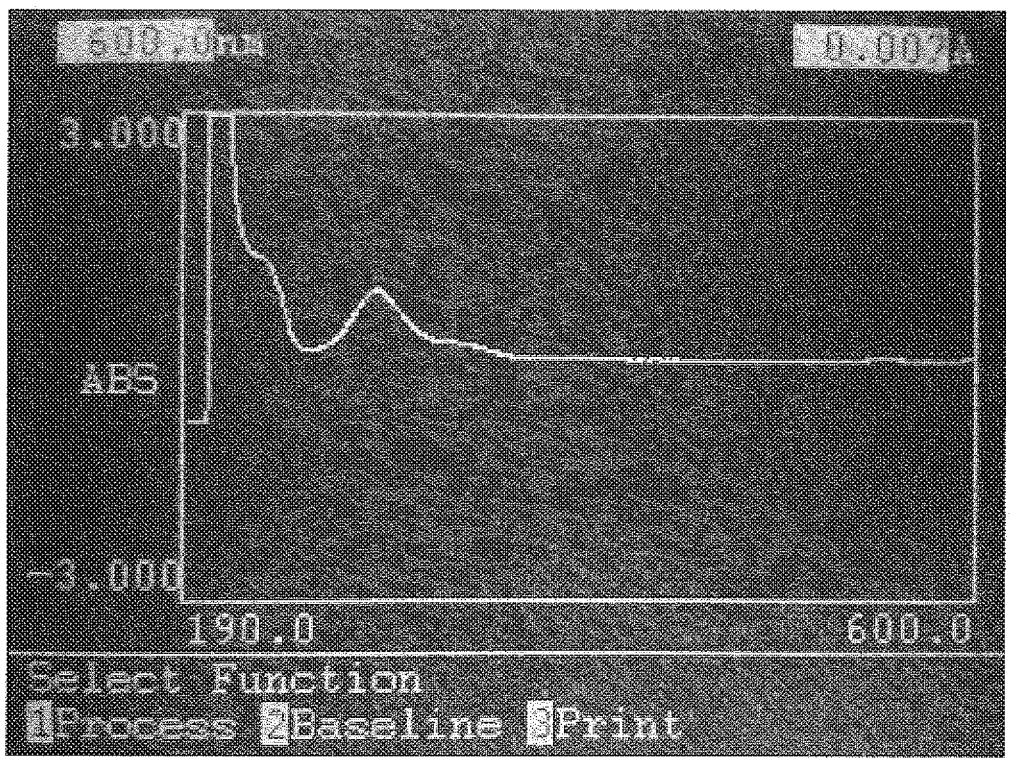
FIG. 1: Reference solution of raw material-UV scanning curve diagram.
Figure 2:
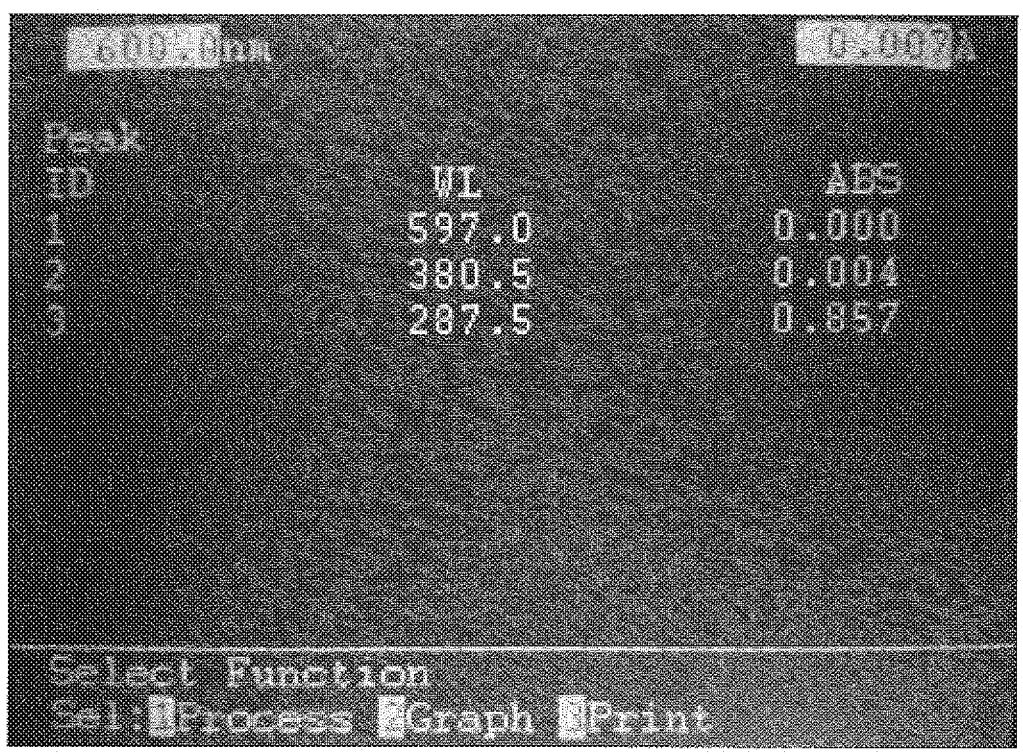
FIG. 2: Reference solution of raw material-UV scanning absorbance list view.
Figure 3:
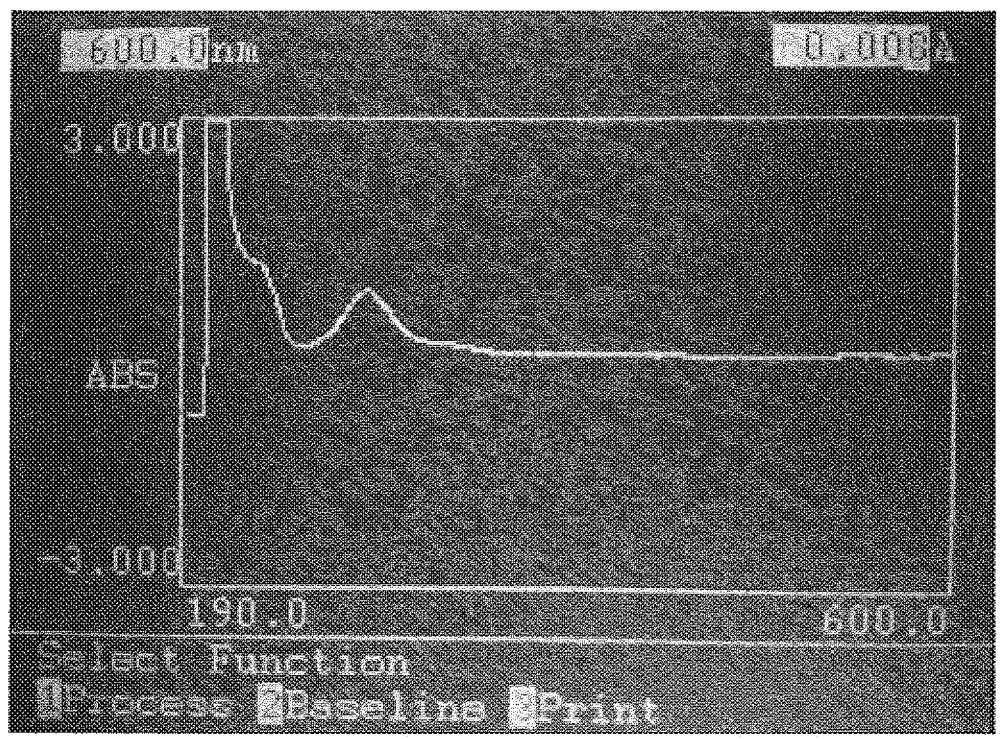
FIG. 3: Test solution of the present invention-UV scanning curve diagram.
Figure 4:
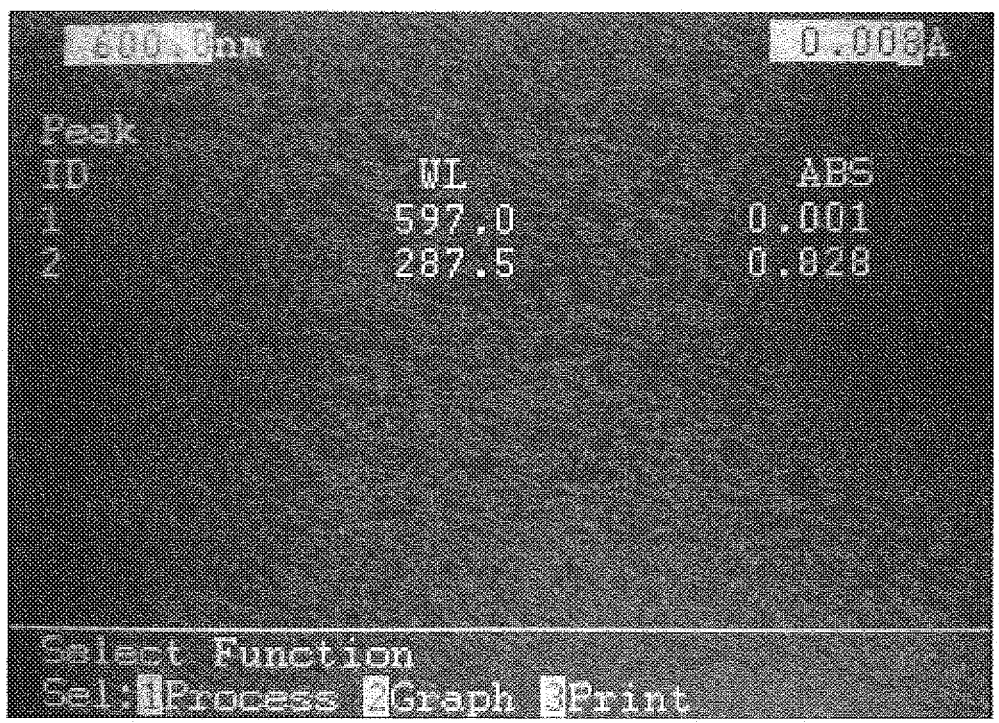
FIG. 4: Test solution of the present invention-UV scanning absorbance list view.

The detailed description of the present invention is given in conjunction with the embodiments, but the implementation of the present invention is not only limited to the disclosed herein.

Embodiment 1: Comparative Research on the Types of Cyclodextrin

The types of cyclodextrin recorded in the Chinese patent application CN200410041364.0 include: β-cyclodextrin, hydroxypropyl-β-cyclodextrin, hydroxyethyl-β-cyclodextrin, methyl-β-cyclodextrin, glucosyl-β-cyclodextrin and sulfonyl-β-cyclodextrin. The cyclodextrin adopted in the present invention is sulfobutylether-β-cyclodextrin and is a specific inclusion material for the present invention. In contrast tests, silybin injections containing different types of cyclodextrin are respectively prepared by adopting the same formulation constituents, formulation dosage and preparation process. Standing is preformed at room temperature for one-week, and the inclusion stability of the injections is observed with the passage of time, that is, the time of medicine precipitation is regarded as a study index to screen the types of cyclodextrin.

(1) Test Method

Weighing 20 g of silybin, 1 g of distearoyl phosphatidylethanolamine-polyethylene glycol 2000 (DSPE-MPEG2000) and 200 g of polyethylene glycol 400, mixing them together, and heating and stirring the mixture at the temperature of 55° C. to make it dissolve, to obtain an organic phase; weighing 50 g of cyclodextrin of the types respectively and putting them in 1000 ml of water for injection, and stirring the mixture to make it dissolve, to obtain different types of cyclodextrin aqueous solutions as aqueous phases (when preparation is performed according to the proportion, the β-cyclodextrin cannot completely dissolve in water, and therefore the β-cyclodextrin is abandoned); stirring and mixing the organic phase with the aqueous phases to obtain about 2 mg/ml of inclusion solutions, removing bacteria using a 0.22 μm filter element and filtering the inclusion solutions; and sub-packaging on the filtrates in 5 ml bottles to obtain silybin injections containing six different types of cyclodextrin.

Allow the injections to stand at room temperature for one week, and respectively observe the inclusion stability of the injections over time, i.e., study the influence of different types of cyclodextrins on the inclusion stability of silybin.

(2) Test Results

TABLE 1

Results of study on inclusion stability of silybin using different types of cycloclextrin

| Type of Cyclodextrin | 1 day | 2 days | 3 days | 4 days | 5 days | 7 days |
|---|---|---|---|---|---|---|
| Hydroxypropyl-β-cyclodextrin | Clear liquid | Clear liquid | Slight turbidity | Obvious turbidity | Obvious turbidity | Precipitation |
| Hydroxyethyl-β-cyclodextrin | Clear liquid | Clear liquid | Clear liquid | Slight turbidity | Obvious turbidity | Precipitation |
| Methyl-β-cyclodextrin | Clear liquid | Slight turbidity | Obvious turbidity | Precipitation | Precipitation | Precipitation |
| Glucosyl-β-cyclodextrin | Clear liquid | Clear liquid | Clear liquid | Slight turbidity | Obvious turbidity | Precipitation |
| Sulfonyl-β-cyclodextrin | Clear liquid | Clear liquid | Clear liquid | Slight turbidity | Obvious turbidity | Obvious turbidity |
| Sulfobutylether-β-cyclodextrin | Clear liquid | Clear liquid | Clear liquid | Clear liquid | Clear liquid | Clear liquid |

Analysis of Results

The silybin injections containing different types of cyclodextrin which are prepared under the conditions of same preparation process and same formulation dosage are completely different in stability at room temperature. The types of cyclodextrin recorded in the Chinese patent application CN200410041364.0 cannot be prepared into stable silybin inclusion compound solutions, the stability time is only kept for 2 to 4 days, but the silybin inclusion compound solution prepared from the sulfobutylether-β-cyclodextrin has no obvious change within at least one week, and actually the solution is quite stable at room temperature. It is verified through a large number of tests that the sulfobutylether-β-cyclodextrin is a relatively optimal inclusion material for the silybin. Therefore, it is the best choice to adopt the sulfobutylether-β-cyclodextrin in the present invention to perform matching inclusion on the silybin.

Embodiment 2: Influence of Organic Solvent for Injection on Quality of Silybin Injection (1) Influence on Quality of Silybin Injection without Organic Solvent for Injection Respectively weighing 100 g, 200 g, 300 g, 400 g and 500 g of sulfobutylether-β-cyclodextrin, and respectively dissolving them to 1000 ml with water for injection, to obtain aqueous solutions containing 10%, 20%, 30%, 40% and 50% of sulfobutylether-β-cyclodextrin; then respectively weighing 1 g of silybin, putting same into the aqueous solutions having the series of different contents of sulfobutylether-β-cyclodextrin, stirring the mixture, and observing the solution states with the passage of time; and by taking appearance and properties as indexes, judging the situation of inclusion of silybin in sulfobutylether-β-cyclodextrin without an organic solvent for injection. The results are as shown in Table 2.

TABLE 2

Influence on quality of silybin injection without organic solvent for injection

| Contents of sulfobutylether-β-cyclodextrin | time | | | |
|---|---|---|---|---|
| | 2 hours | 6 hours | 12 hours | 24 hours |
| 10% | Serious turbidity | Serious turbidity | Serious turbidity | Serious turbidity |
| 20% | Serious turbidity | Serious turbidity | Serious turbidity | Serious turbidity |
| 30% | Serious turbidity | Serious turbidity | Serious turbidity | Serious turbidity |

TABLE 2-continued

Influence on quality of silybin injection
without organic solvent for injection

| Contents of sulfobutylether- | time | | | |
|---|---|---|---|---|
| β-cyclodextrin | 2 hours | 6 hours | 12 hours | 24 hours |
| 40% | Serious turbidity | Serious turbidity | Serious turbidity | Serious turbidity |
| 50% | Serious turbidity | Serious turbidity | Serious turbidity | Serious turbidity |

Analysis of Results

Silybin is directly put into a sulfobutylether-β-cyclodextrin solution, and the mixture is stirred to make it dissolve by a conventional method. The result indicates that when the concentration of sulfobutylether-β-cyclodextrin is within a range of 10% to 50%, the medicine-loading capacity is only 1 mg/ml, and the mixture is stirred for 24 hours, the solution is still turbid without anything dissolved. Thus it can be seen that the physicochemical properties of silybin are relatively special, and a cyclodextrin inclusion compound cannot be prepared with the method of direct addition.

(2) Influence on Quality of Silybin Injection with Organic Solvent for Injection Respectively weighing 100 g, 200 g, 300 g, 400 g and 500 g of sulfobutylether-β-cyclodextrin, and respectively dissolving them to 1000 ml with water for injection, to obtain aqueous solutions containing 10%, 20%, 30%, 40% and 50% of sulfobutylether-β-cyclodextrin; weighing 6 g of silybin and 120 g of polyethylene glycol 400, mixing them together, and heating and stirring the mixture at the temperature of 55° C. to make it dissolve, to obtain an organic phase; respectively weighing 21 g of organic phase, respectively putting same into the aqueous solutions having the series of different contents of sulfobutylether-β-cyclodextrin, stirring the mixture, and observing the solution states with the passage of time; and by taking appearance, and properties as indexes, judging the situation of inclusion of silybin in sulfobutylether-β-cyclodextrin with an organic solvent for injection. The results are as shown in Table 3.

TABLE 3

Influence on quality of silybin injection
with organic solvent for injection

| Contents of sulfobutylether- | Time | | | |
|---|---|---|---|---|
| β-cyclodextrin | 2 hours | 6 hours | 12 hours | 24 hours |
| 10% | Substantially clear liquid with several fine particles suspended | Substantially clear liquid with several fine particles suspended | Substantially clear liquid with several fine particles suspended | Substantially clear liquid with several fine particles suspended |
| 20% | Substantially clear liquid with several fine particles suspended | Substantially clear liquid with several fine particles suspended | Substantially clear liquid with several fine particles suspended | Substantially clear liquid with several fine particles suspended |
| 30% | Substantially clear liquid with several fine particles suspended | Substantially clear liquid with several fine particles suspended | Substantially clear liquid with several fine particles suspended | Substantially clear liquid with several fine particles suspended |
| 40% | Substantially clear liquid with several | Substantially clear liquid with several | Substantially clear liquid with several | Substantially clear liquid with several |

TABLE 3-continued

Influence on quality of silybin injection
with organic solvent for injection

| Contents of sulfobutylether- | Time | | | |
|---|---|---|---|---|
| β-cyclodextrin | 2 hours | 6 hours | 12 hours | 24 hours |
| | fine particles suspended | fine particles suspended | fine particles suspended | fine particles suspended |
| 50% | Substantially clear liquid with several fine particles suspended | Substantially clear liquid with several fine particles suspended | Substantially clear liquid with several fine particles suspended | Substantially clear liquid with several fine particles suspended |

Analysis of Results

Silybin is dissolved in an organic solvent for injection; and then, is injected into a sulfobutylether-β-cyclodextrin solution to prepare an inclusion compound. Compared with the serious turbidity without the organic solvent for injection, for the achieved solution state, the clarity is significantly increased. It is thus clear that the organic solvent for injection in the formulation can better wrap silybin in sulfobutylether-β-cyclodextrin molecules, thus significantly improving the wrapping effect. Although a minute quantity of medicine in the solution is not wrapped, this problem is solved through the addition of an appropriate amount of cosolvent (See embodiment 3). Therefore, the organic solvent for injection in the formulation must be matched to combine the specific physicochemical properties of silybin, which is one of the important technical features of the present invention, otherwise, wrapping would not be realized.

Embodiment 3: Influence of Cosolvent on Preparation of Silybin Injection

On one hand, the cosolvent in the formulation is used to solve the problem that wrapping is not complete when an inclusion compound is prepared, namely the phenomenon that several fine particles are suspended in the solution mentioned in embodiment 2; on the other hand, the addition of the cosolvent can ensure that a freeze-dried sample has good re-dissolution properties. Consequently, the cosolvent enables die silybin injection prepared by the present invention to have more reliable quality. During the contrast test, with the same formulation constituents and dosage, the influences with and without the addition of the cosolvent on the quality of the silybin injection are studied, which is explained by taking the cosolvent, i.e. distearoyl phosphatidylethanolamine-polyethylene glycol 2000 (DSPE-MPEG2000) as an example.

(1) Preparation Method of Silybin Injection without Cosolvent and Results

Weighing 2 g of silybin and 20 g of polyethylene glycol 400, mixing them together, and heating and stirring the mixture at the temperature of 55° C. to make it dissolve, to obtain an organic phase; weighing 50 g of sulfobutylether-β-cyclodextrin and 50 g of mannitol, dissolving them to 1000 ml by adding water for injection, and stirring the mixture to make it dissolve, to obtain an aqueous phase; stirring and mixing the organic phase with the aqueous phase to obtain an inclusion solution; removing bacteria using a 0.22 μm filter element, filtering the inclusion solution, and measuring intermediates, that is, observing the solution states and the marked percentage contents of medicines before and after filtration by taking samples; and performing sub-packaging an the filtrate in 5 ml bottles, freeze-drying and sealing. After freeze-drying, adding water for injection for re-dissolution; observing the solution state with a light detector, and filtering the re-dissolution solution using a 0.22 μm filter film; and measuring the marked percentage contents of medicines in the subsequent filtrate. The results are as shown in Table 4.

TABLE 4

Results of silybin injection without cosolvent

| Items | Solution states | Marked content percentages |
|---|---|---|
| Inclusion solution before filtration | Substantially clear liquid with a few fine particles suspended | 99.76% |
| Inclusion solution after filtration | Completely clear liquid | 97.07% |
| After freeze-drying and re-dissolution | Obvious suspension of fine particles, showing opalescence | 95.33% |

Analysis of Results

Without a cosolvent, some medicines cannot be wrapped completely in the preparation process; and the bacterium removal and filtration are not smooth in the presence of a relatively large resistance force, and therefore medicines are retained. All this is not conducive to mass production. Moreover, the complete re-dissolution cannot be realized after freeze-drying.

(2) Preparation of Inclusion Solution with Cosolvent

Weighing 2 g of silybin, 0.1 g of distearoyl phosphatidylethanolamine-polyethylene glycol 2000 (DSPE-MPEG2000) and 20 g of polyethylene glycol 400, mixing them together, and heating and stirring the mixture at the temperature of 55° C. to make it dissolve, to obtain an organic phase; weighing 50 g of sulfobutylether-β-cyclodextrin and 50 g of mannitol, dissolving them to 1000 ml by adding water for injection, and stirring the mixture to make it, to obtain an aqueous phase; stirring and mixing the organic phase with the aqueous phase to obtain an inclusion solution; removing bacteria using a 0.22 μm filter element, filtering the inclusion solution, and measuring intermediates, that is, observing the solution states and the marked percentage contents of medicines before and after filtration by taking samples; and performing sub-packaging on the filtrate in 5 ml bottles, freeze-drying and sealing. After freeze-drying, adding water for injection for re-dissolution; observing the solution state with a light detector, and filtering the re-dissolution solution using a 0.22 μm filter film; and measuring the marked percentage contents of medicines in the subsequent filtrate. The results are as shown in Table 5.

TABLE 5

Results of silybin injection with cosolvent

| Items | Solution states | Marked content percentages |
|---|---|---|
| Inclusion solution before filtration | Completely clear liquid | 100.04% |
| Inclusion solution after filtration | Completely clear liquid | 99.92% |
| After freeze-drying and re-dissolution | Completely clear liquid | 99.78% |

Analysis of Results

After a cosolvent is added, the medicine is fully coated in the preparation process, bacterium removal and filtration are operated smoothly, no obvious change is generated in the content of the medicine before filtration and after filtration, and the medicine can be completely re-dissolved after being freeze-dried, so that adding the cosolvent into the formulation is an important technical feature of the present invention.

Embodiment 4: A Silybin Injection

Weighing 2 g of silybin, 0.1 g of distearoyl phosphatidylethanolamine-polyethylene glycol 2000 (DSPE-MPEG2000) and 20 g of polyethylene glycol 400, mixing them together, and heating and stirring the mixture at the temperature of 55° C. to make it dissolve, to obtain an organic phase; weighing 40 g of sulfobutylether-β-cyclodextrin and 60 g of mannitol, putting them into 800 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing to obtain a silybin freeze-dried powder for injection.

Embodiment 5: A Silybin Injection

Weighing 2 g of silybin, 0.1 g of distearoyl phosphatidylethanolamine-polyethylene glycol 2000 (DSPE-MPEG2000) and 20 g of polyethylene glycol 400, mixing them together, heating and stirring the mixture at the temperature of 55° C. to make it dissolve, to obtain an organic phase; weighing 40 g of sulfobutylether-β-cyclodextrin, putting same into 900 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid; adding 1 g of activated carbon for injection to perform adsorption for 30 minutes, and then filtering the solution to remove carbon through a 1 μm titanium rod and removing bacteria through a 0.22 μm filter element; and performing sub-packaging and sealing to obtain a silybin injection.

Embodiment 6: A Silybin Injection

Weighing 10 g of silybin, 10 g of distearoyl phosphatidylethanolamine-polyethylene glycol 2000 (DSPE-MPEG2000) and 100 g of polyethylene glycol 400, mixing them together, and heating and stirring the mixture at the temperature of 60° C. to make it dissolve, to obtain an organic phase; weighing 300 g of sulfobutylether-β-cyclodextrin, 50 g of xylitol, 50 g of sorbitol and 100 g of mannitol, putting them into 350 ml of water fin injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 8.00 using potassium dihydrogen phosphate and dipotassium hydrogen phosphate; adding 5 g of activated carbon for injection to perform adsorption for 15 minutes, and then filtering the solution to remove carbon through a 1 μm titanium rod and removing bacteria through a 0.22 μm filter element; and performing sub-packaging, freeze-drying and scaling to obtain a silybin freeze-dried powder for injection.

Embodiment 7: A Silybin Injection

Weighing 8 g of silybin, 5 g of distearoyl phosphatidylethanolamine-polyethylene glycol 2000 (DSPE-MPEG2000) and 50 g of polyethylene glycol 50, mixing them together, and heating and stirring the mixture at the temperature of 70° C. to make it dissolve, to obtain an organic phase; weighing 200 g of sulfobutylether-β-cyclodextrin, 50 g of sucrose and 100 g of mannitol, putting them into 550 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 7.00 using sodium dihydrogen phosphate and disodium hydrogen phosphate; adding 3 g of activated carbon for injection to perform adsorption for 20 minutes, then filtering the solution to remove carbon through a 1 μm titanium rod and removing bacteria through a 0.22 μm filter element; and performing sub-packaging, freeze-drying and sealing to obtain a silybin freeze-dried powder for injection.

Embodiment 8: A Silybin Injection

Weighing 5 g of silybin, 3 g of distearoyl phosphatidylethanolamine-polyethylene glycol 2000 (DSPE-MPEG2000) and 20 g of polyethylene glycol 400, mixing them together, and heating and stirring the mixture at the temperature of 50° C. to make it dissolve, to obtain an organic phase; weighing 100 g of sulfobutylether-β-cyclodextrin, 40 g of trehalose and 60 g of mannitol, putting them into 700 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 2.00 using hydrochloric acid and citric acid; adding 2 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing to obtain a silybin freeze-dried powder for injection.

Embodiment 9: A Silybin Injection

Weighing 0.5 g of silybin, 0.01 g of distearoyl phosphatidylethanolamine-polyethylene glycol 2000 (DSPE-MPEG2000) and 5 g of polyethylene glycol 400, mixing them together, heating and stirring the mixture at the temperature of 40° C. to make it dissolve, to obtain an organic phase; weighing 20 g of sulfobutylether-β-cyclodextrin, and putting same into 950 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 6.00 using phosphoric acid and dipotassium hydrogen phosphate; adding 0.5 g of activated carbon for injection to perform adsorption for 60 minutes, then filtering the solution to remove carbon through a 1 μm titanium rod and removing bacteria through a 0.22 μm filter element; and performing sub-packaging and sealing to obtain silybin injection.

Embodiment 10: A Silybin Injection

Weighing 1 g of silybin and 10 g of polyethylene glycol 400, mixing them together, and heating and stirring the mixture at the temperature of 50° C. to make it dissolve, to obtain an organic phase; weighing 30 g of sulfobutylether-β-cyclodextrin and 40 g of mannitol, putting same into 900 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 2.50 using hydrochloric acid, citric acid and disodium citrate; adding 1 g of activated carbon for injection to perform adsorption for 40 minutes, and then filtering the solution to remove carbon through a 1 μm titanium rod and removing bacteria through a 0.22 μm filter clement; and performing sub-packaging, freeze-drying and sealing to obtain a silybin freeze-dried powder for injection.

Embodiment 11: A Silybin Injection

Weighing 1 g of silybin, 0.05 g of distearoyl phosphatidylethanolamine-polyethylene glycol 2000 (DSPE-MPEG2000) and 10 g of polyethylene glycol 400, mixing them together, and heating and stirring the mixture at the temperature of 55° C. to make it dissolve, to obtain an organic phase; weighing 20 g of sulfobutylether-β-cyclodextrin, 20 g of lactose and 10 g of dextran 70, putting them into 900 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 5.00 using phosphoric acid and sodium dihydrogen phosphate; adding 1 g of activated carbon for injection to perform adsorption for 30 minutes, then filtering the solution to remove carbon through an 1 μm titanium rod and removing bacteria through a 0.22 μm filter element; and performing sub-packaging freeze-drying and sealing to obtain a silybin freeze-dried powder for injection.

Embodiment 12: A Silybin Injection

Weighing 1 g of silybin, 0.2 g of distearoyl phosphatidylethanolamine-polyethylene glycol 2000 (DSPE-MPEG2000) and 10 g of polyethylene glycol 400, mixing them together, and heating and stirring the mixture at the temperature of 55° C. to make it dissolve, to obtain an organic, phase; weighing 20 g of sulfobutylether-β-cyclodextrin, 20 g of lactose and 10 g of dextran 20, putting them into a 900 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 4.50 using glacial acetic acid and sodium acetate; adding 1 g of activated carbon for injection to perform adsorption for 30 minutes, and then filtering the solution to remove carbon through 1 μm titanium rod and removing bacteria through a 0.22 μm filter element; and performing sub-packaging, freeze-drying and sealing to obtain a silybin freeze-dried powder for injection.

Embodiment 13: A Silybin Injection

Weighing 1 g of silybin, 0.1 g of distearoyl phosphatidylethanolamine-polyethylene glycol 2000 (DSPE-MPEG2000) and 20 g of absolute ethyl alcohol, mixing them together, and heating and stirring the mixture at the temperature of 55° C. to make it dissolve, to obtain an organic phase; weighing 30 g of sulfobutylether-β-cyclodextrin and 40 g of mannitol, putting them into 900 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid and trisodium citrate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing to obtain a silybin freeze-dried powder for injection.

Embodiment 14: A Silybin Injection

Weighing 1 g of silybin, 0.1 g of distearoyl phosphatidylethanolamine-polyethylene glycol 2000 (DSPE-MPEG2000) and 20 g of propylene glycol, mixing them together, and heating and stirring the mixture at the temperature of 55° C. to make it dissolve, to obtain an organic phase; weighing 30 g of sulfobutylether-β-cyclodextrin and 40 g of mannitol, putting them into 900 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid and trisodium citrate; adding 1 g of activated carbon for injection is added to perform adsorption for 30 minutes, and then filtering the solution to remove carbon through a 1 μm titanium rod and removing bacteria through a 0.22 μm filter element; and performing sub-packaging, freeze-drying and sealing to obtain a silybin freeze-dried powder for injection.

Embodiment 15: A Silybin Injection

Weighing 2 g of silybin, 1 g of distearoyl phosphatidylethanolamine-polyethylene glycol 2000 (DSPE-MPEG2000) and 40 g of absolute ethyl alcohol, mixing them together, and heating and stirring the mixture at the temperature of 55° C. to make it dissolve, to obtain an organic phase; weighing 40 g of sulfobutylether-β-cyclodextrin and 60 g lactose, putting them into 800 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid and disodium hydrogen phosphate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 16: A Silybin Injection

Weighing 2 g of silybin, 1 g of distearoyl phosphatidylethanolamine-polyethylene glycol 2000 (DSPE-MPEG2000) and 40 g of propylene glycol, mixing them together, and heating and stirring the mixture at the temperature of 55° C. to make it dissolve; to obtain an organic phase; weighing 40 g of sulfobutylether-β-cyclodextrin and 60 g of lactose, putting them into 800 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid and disodium hydrogen phosphate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 17: A Silybin Injection

Weighing 2 g of silybin, 0.2 g of distearoyl phosphatidylethanolamine-polyethylene glycol 2000 (DSPE-MPEG2000) and 50 g of polyethylene glycol 400, mixing them together, and heating and stirring the mixture at the temperature of 55° C. to make it dissolve, to obtain an organic phase; weighing 50 g of sulfobutylether-β-cyclodextrin and 60 g of dextran 40, putting them into 800 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be. 3.50 using citric acid and trisodium citrate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 18: A Silybin Injection

Weighing 2 g of silybin, 0.4 g of distearoyl phosphatidylethanolamine-polyethylene glycol 2000 (DSPE-MPEG2000) and 20 g of polyethylene glycol 400, mixing them together, and heating and stirring the mixture at the temperature of 55° C. to make it dissolve, to obtain an organic phase; Weighing 30 g of sulfobutylether-β-cyclodextrin, 30 g of dextran 40 and 20 g of lactose, putting them into 850 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.00 using citric acid; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 19: A Silybin Injection

Weighing 2 g of silybin, 0.1 g of distearoyl phosphatidylethanolamine-polyethylene glycol 2000 (DSPE-MPEG2000) and 30 g of polyethylene glycol 400, mixing them together, heating and stirring the mixture at the temperature of 55° C. to make it dissolve, to obtain an organic phase; weighing 40 g of sulfobutylether-β-cyclodextrin and 60 g of mannitol, putting them into 850 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.00 using citric acid and trisodium citrate; adding g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 20: A Silybin Injection

Weighing 2 g of silybin, 0.5 g of distearoyl phosphatidylethanolamine-polyethylene glycol 2000 (DSPE-MPEG2000) and 20 g of polyethylene glycol 400, mixing them together, and heating and stirring the mixture at the temperature of 55° C. to make it dissolve, to obtain an organic phase; weighing 40 g of sulfobutylether-β-cyclodextrin and 50 g of mannitol, putting them into 850 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 4.00 using citric acid and trisodium citrate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 21: A silybin injection

Weighing 2 g of silybin, 10 g of polysorbate 80 and 20 g of polyethylene glycol 400, mixing them together, and heating and stirring the mixture at the temperature of 55° C. to make it dissolve, to obtain an organic phase; weighing 40 g of sulfobutylether-β-cyclodextrin and 70 g of mannitol, putting them into 850 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 4.00 using citric acid and trisodium citrate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 22: A Silybin Injection

Weighing 2 g of silybin, 10 g of polyoxyethylated castor oil and 20 g of polyethylene glycol 400, mixing them together, and heating and stirring the mixture at the temperature of 55° C. to make it dissolve, to obtain an organic phase; weighing 110 g of sulfobutylether-β-cyclodextrin, putting same into 850 ml of water for injection, and stirring the mixture to make it dissolve, to obtain an aqueous phase; mixing the organic phase with the aqueous phase uniformly and diluting with water for injection to 1000 ml, to obtain a medicine solution; regulating the pH value of the medicine solution to be 4.00 using citric acid and trisodium citrate; adding 1 g of activated carbon for injection to perform, adsorption for 30 minutes, and then filtering the solution to remove carbon through a 1 μm titanium rod and removing bacteria through a 0.22 μm filter element; and performing sub-packaging and sealing, to obtain a silybin injection.

Embodiment 23: A silybin injection

Weighing 2 g of silybin, 10 g of poly(ethylene glycol)-block-poly(propylene glycol)-block-poly(ethylene glycol) 188 and 20 g of polyethylene glycol 400, mixing them together, and heating and stirring the mixture at the temperature of 55° C. to make it dissolve, to obtain an organic phase; weighing 40 g of sulfobutylether-β-cyclodextrin, 20 g of lactose and 40 g of mannitol, putting them into 800 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 5.00 using phosphoric acid and sodium dihydrogen phosphate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 24: A silybin injection

Weighing 2 g of silybin, 5 g of polysorbate 80 and 20 g of polyethylene glycol 400, mixing them together, and heating and stirring the mixture at the temperature of 55° C. to make it dissolve, to obtain an organic phase; weighing 450 g of sulfobutylether-β-cyclodextrin, and putting same into 400 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 5.00 using phosphoric acid and disodium hydrogen phosphate; adding 1 g of activated carbon for injection to perform adsorption for 30 minutes, and then filtering the solution to remove carbon through a 1 μm titanium rod and removing bacteria through a 0.22 μm filter element; and performing sub-packaging and sealing, to obtain a silybin injection.

Embodiment 25: A Silybin Injection

Weighing 2 g of silybin, 5 g polyoxyethylated castor oil, 5 g of propylene glycol and 15 g of absolute ethyl alcohol, mixing them together, and heating and stirring the mixture at the temperature of 55° C. to make it dissolve, to obtain an organic phase; weighing 100 g of sulfobutylether-β-cyclodextrin, putting same into water for injection of 850 ml, stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid; adding 1 g of activated carbon for injection to perform adsorption for 30 minutes, and then filtering the solution to remove carbon through a 1 μm titanium rod and removing bacteria through a 0.22 μm filter element; and performing sub packaging and sealing, to obtain a silybin injection.

Embodiment 26: A Silybin Injection

Weighing 2 g of silybin, 0.2 g of distearoyl phosphatidylethanolamine-polyethylene glycol 2000 (DSPE-MPEG2000) and 20 g of polyethylene glycol 200, mixing them together, and heating and stirring the mixture at the temperature of 55° C. to make it dissolve, to obtain an organic phase; weighing 40 g of sulfobutylether-β-cyclodextrin and 60 g of mannitol, putting them into 850 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.00 using citric acid; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 27: A Silybin Injection

Weighing 2 g of silybin, 0.1 g of distearoyl phosphatidylethanolamine-polyethylene glycol 2000 (DSPE-MPEG2000) and 20 g of polyethylene glycol 300, mixing them together, and heating and stirring the mixture at the temperature of 60° C. to make it dissolve, to obtain an organic phase; weighing 40 g of sulfobutylether-β-cyclodextrin and 50 g of mannitol, putting them into 850 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid and sodium citrate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 28: A Silybin Injection

Weighing 2 g of silybin, 0.1 g of distearoyl phosphatidylethanolamine-polyethylene glycol 2000 (DSPE-MPEG2000) and 30 g of polyethylene glycol 600, mixing them together, and heating and stirring the mixture at the temperature of 55° C. to make it dissolve, to obtain an organic phase; weighing 50 g of sulfobutylether-β-cyclodextrin and 60 g of mannitol, putting them into 800 ml of Water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 29: A Silybin Injection

Weighing 2 g of silybin, 0.05 g of distearoyl phosphatidylethanolamine-polyethylene glycol 2000 (DSPE-MPEG2000) and 20 g of polyethylene glycol 400, mixing them together, and heating and stirring the mixture at the temperature of 55° C. to make it dissolve, to obtain an organic phase; weighing 50 g of sulfobutylether-β-cyclodextrin, 30 g of lactose and 30 g of mannitol, putting them into 850 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid and trisodium citrate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 30: A Silybin Injection

Weighing 3 g of silybin, 2 g of distearoyl phosphatidylethanolamine-polyethylene glycol 2000 (DSPE-MPEG2000) and 20 g of polyethylene glycol 400, mixing them together, and heating and stirring the mixture at the temperature of 60° C. to make it dissolve, to obtain an organic phase; weighing 80 g of sulfobutylether-β-cyclodextrin, 40 g of dextran 40 and 60 g of mannitol, putting them into 750 ml of water for injection, and stirring the mixture to make it dissolve, to obtain an aqueous phase; mixing the organic phase with the aqueous phase uniformly, and diluting with water for injection to 1000 ml, obtain a medicine solution; regulating the pH value of the medicine solution to be 3.50 using citric acid; adding 1 g activated carbon for injection to perform adsorption for 50 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 31: A Silybin Injection

Weighing 3 g of silybin, 3 g of distearoyl phosphatidylethanolamine-polyethylene glycol 2000 (DSPE-MPEG2000), 25 g of propylene glycol and 5 g of polyethylene glycol 400, mixing then) together, and heating and stirring the mixture at the temperature of 55° C. to make it dissolve, to obtain an organic phase; weighing 50 g of sulfobutylether-β-cyclodextrin and 60 g of mannitol, putting them into 800 ml of water for injection, and stirring the mixture to make it dissolve, to obtain an aqueous phase; mixing the organic phase with the aqueous phase it dissolve so as to obtain an aqueous phase; mixing the organic phase with the aqueous phase, and diluting with water for injection to 1000 ml, to obtain a medicine solution; regulating the pH value of the medicine solution to be 3.50 using citric acid; adding 1 g of activated carbon for injection to perform adsorption for 40 minutes, and then filtering the solution to remove carbon through a 1 μm titanium rod and removing bacteria through a 0.22 μm filter element; and performing sub-packaging, freeze-drying and sealing, to obtain a silybin freeze-dried powder for injection.

Embodiment 32: A Silybin Injection

Weighing 3 g of silybin, 1 g of distearoyl phosphatidylethanolamine-polyethylene glycol 2000 (DSPE-MPEG2000) and 30 g of polyethylene glycol 400 mixing them together, and heating and stirring the mixture at the temperature of 55° C. to make it dissolve, to obtain an organic phase; weighing 60 g of sulfobutylether-β-cyclodextrin and 60 g of mannitol, putting them into 800 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid and trisodium citrate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze-drying and sealing, to obtain a silybin freeze-drier powder for injection.

Embodiment 33: A Silybin Injection

Weighing 4 g of silybin, 1 g of distearoyl phosphatidylethanolamine-polyethylene glycol 2000 (DSPE-MPEG2000), 10 g of absolute ethyl alcohol, 10 g of propylene glycol and 20 g of polyethylene glycol 400, mixing them together, and heating and stirring the mixture at the temperature of 55° C. to make it dissolve, to obtain an organic phase; weighing 80 g of sulfobutylether-β-cyclodextrin and 100 g of mannitol, putting them into 750 ml of water fin injection, and stilling the mixture to make it dissolve, to obtain an aqueous phase; mixing the organic phase with aqueous phase uniformly, and diluting with water for injection to 1000 ml, to obtain a medicine solution; regulating the pH value of the medicine solution to be 6.00 using sodium dihydrogen phosphate and dipotassium hydrogen phosphate; adding 1 g of activated carbon for injection to perform adsorption for 30 minutes, and then filtering the solution to remove carbon through a 1 μm titanium rod and removing bacteria through a 0.22 μm filter element; and performing sub-packaging, freeze drying and sealing, to obtain a silybin freeze-dried powder for injection.

Embodiment 34: A Silybin Injection

Weighing 2 g of silybin, 0.1 g of distearoyl phosphatidylethanolamine-polyethylene glycol 2000 (DSPE-MPEG2000) and 20 g of polyethylene glycol 400, mixing them together, and heating and stirring the mixture at the temperature of 55° C. to make it dissolve, to obtain an organic phase; weighing 500 g of sulfobutylether-β-cyclodextrin, putting same in 400 ml of water for injection, and stirring the mixture to make it dissolve, to obtain an aqueous phase; mixing the organic phase with the aqueous phase uniformly, and diluting with water for injection to 1000 ml, to obtain a medicine solution; regulating the pH value of the medicine solution to be 3.50 using citric acid; adding 1 g of activated carbon for injection to perform for 30 minutes, and then filtering the solution to remove carbon through a 1 μm titanium rod and removing bacteria through a 0.22 μm filter element; and performing sub-packaging and sealing, to obtain a silybin injection.

Embodiment 35: Study on Dilution Stability of Silybin Injection

The silybin injections prepared in embodiment 4, embodiment 6, embodiment 9, embodiment 13, embodiment 17 and embodiment 32 are taken, wherein the freeze-dried powder for injection is re-dissolved to a concentration of the solution before freeze-drying with normal saline. The re-dissolution solutions of the silybin injection and freeze-dried powder for injection are respectively diluted by ten times with normal saline to obtain diluted solution. The diluted solution is placed at the room temperature and sampled as time changes, and filtered with 0.45 μm filtering film, so that the changes of the silybin content in the subsequent filtrate with time are determined to study the dilution stability of the silybin injection.

Chromatographic conditions: Octadecylsilane chemically bonded silica is used as a filler; methanol-water-glacial acetic acid (48:52:1) is used as a mobile phase; the column temperature is 40° C.; and the detection wavelength is 288 nm.

Determination method: 1 ml of diluted solution is accurately measured and diluted to 10 ml with the mobile phase to be used as a test solution; 10 μl of the test solution is accurately measured and injected into a liquid chromatography, and the peak area is recorded; by taking the peak area at 0 hour as 100%, the changes of the peak area percentages with time are calculated, and the results are shown in table 6:

TABLE 6

Results of study on dilution stability of silybin injection

| Samples | 0 hour | 8 hours | 12 hours | 16 hours | 20 hours | 24 hours |
|---|---|---|---|---|---|---|
| Embodiment 4 | 100% | 100.2% | 100.4% | 99.8% | 99.6% | 98.8% |
| Embodiment 6 | 100% | 99.7% | 100.1% | 99.6% | 99.2% | 99.5% |
| Embodiment 9 | 100% | 99.9% | 99.7% | 100.3% | 100.0% | 99.2% |
| Embodiment 13 | 100% | 99.9% | 100.2% | 100.1% | 99.8% | 99.6% |
| Embodiment 17 | 100% | 101.0% | 100.3% | 100.7% | 99.7% | 100.1% |
| Embodiment 32 | 100% | 100.5% | 99.6% | 98.9% | 99.7% | 99.1% |

The results indicate that, the dilution stability of the silybin injection of the present invention in the normal saline before clinical medication is more than 24 hours, so that it can fully meet the clinical medication requirements.

Embodiment 36: Verification Performed on Preparation Method Recorded in Chinese Patent Application CN02125823.6

The Chinese patent application CN02125823.6 with the title "silymarin injection containing cyclodextrin or derivatives thereof" and the publication number of CN1391894A, according to the implementing scheme recorded in the Description, has the key technical features of adding silymarin into an aqueous solution containing cyclodextrin, regulating the pH of the solution to alkalinity using sodium hydroxide to dissolve silybin, and after dissolution, regulating the pH value to be 6.0 to 6.5 using hydrochloric acid to obtain a silymarin cyclodextrin inclusion compound. During verification, the silymarin is replaced with silybin, and the verification is strictly performed according to the implementing scheme described in embodiment 1 of the patent.

(1) Preparation Method (the Same as that in Embodiment 1 of the Original Patent)

Dissolving 3 g of hydroxypropyl-β-cyclodextrin in 10 ml of water for injection, adding 300 mg of silybin, regulating the pH value to be 10 with 1N of NaOH solution, continuously stirring for 5 hours to dissolve the silybin, regulating the pH to be 6.5 with 1N of HCl solution, and performing filtration, bacterium removal, sub-packaging, freeze-drying and sealing, to obtain a silybin freeze-dried powder for injection.

(2) Experiment Phenomena and Results

① Discoloration

In the process of regulating the pH value to be 10 with NaOH solution and of stirring to make silybin dissolve, it is found that the solution changes gradually from the original off-white suspension into a green yellow solution and into a deep yellow clear solution finally. However, for the preparation method of the present invention, the discoloration phenomenon is not found in the whole preparation process.

② Verification of Destructiveness caused by NaOH to Silybin

When NaOH solution is used to regulate the pH value to be 10 to make silybin dissolve, the obtained solution shows significant changes in color. The analysis of causes indicates that it is possible that NaOH, as a strong base, has destructive effects on the structure of silybin, thus causing the color of the solution to change. Therefore, we perform ultraviolet scanning on alkaline solution to study whether new absorption peaks appear, whereby determining whether NaOH has destructive effects on silybin.

Reference Solution of Raw Material:

An appropriate amount of silybin raw medicine is taken, and dissolved and diluted with methanol to obtain the reference solution of raw material;

Test Solution of Contrastive Patent:

An appropriate amount of the above-mentioned medicine solution in which NaOH solution is used for regulation to make silybin dissolve is taken, and is diluted with water to obtain a test solution of contrastive patent.

Test Solution of the Present Invention:

The medicine solution of embodiment 4 of the present invention is taken, and is diluted with water to obtain a test solution of the present invention.

Figure 5:
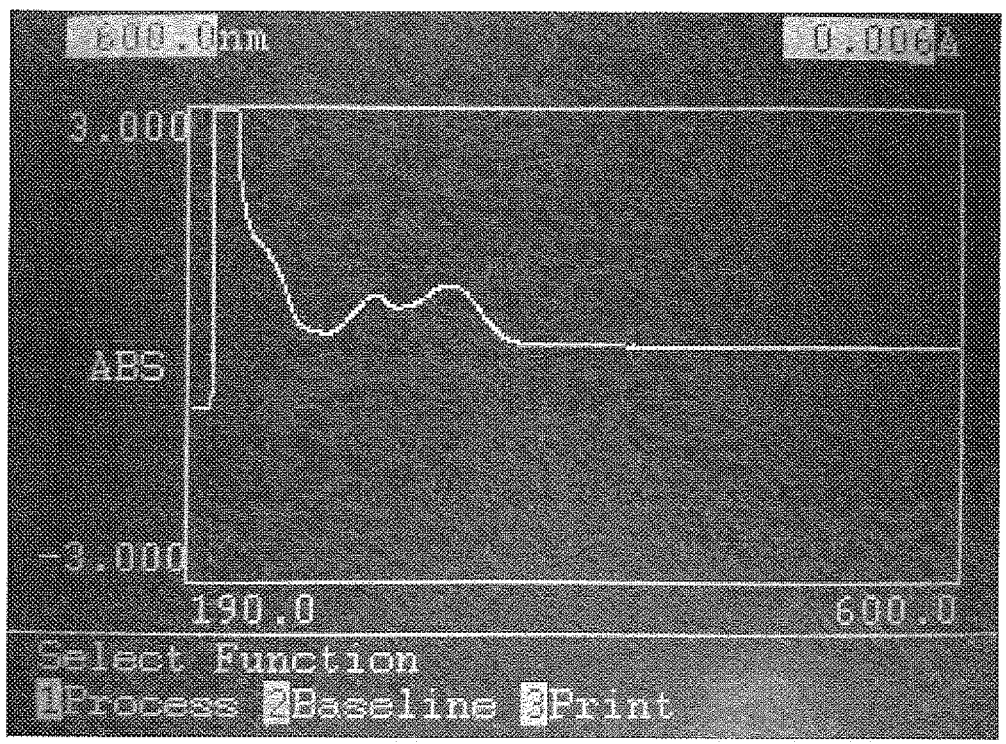
FIG. 5: Test solution of the contrastive patent-UV scanning curve diagram.
Figure 6:
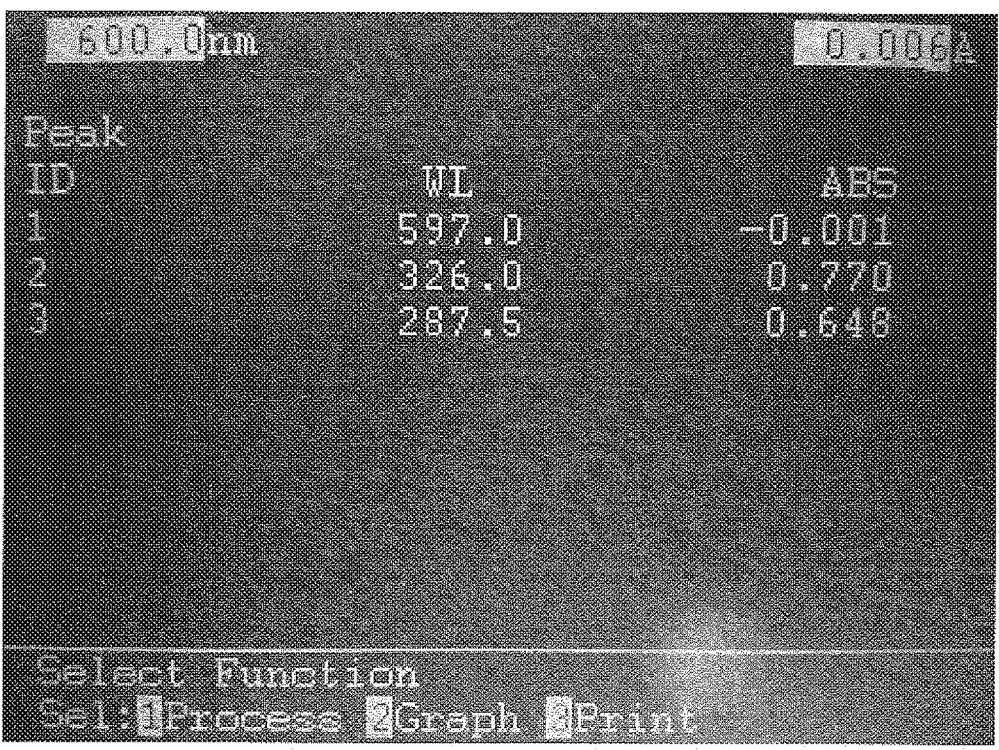
FIG. 6: Test solution of the contrastive patent-UV scanning absorbance list view.

The above-mentioned solutions are scanned within the wavelength of 190-600 nm respectively. The results indicate that both the reference solution of raw material and the test solution of the present invention have the maximum absorption at 287.5 nm, and almost have no absorption at the rest of wavelengths (see FIGS. 1-4); however, in addition to having relatively large absorption at 287.5 nm, the test solution of contrastive patent also has a larger absorption peak at 326.0 nm (see FIGS. 5 and 6). This indicates that under the action of NaOH, the structure of silybin changes significantly, while the quality of the medicine solution prepared by the present invention is stable. Therefore, there are certain problems in the quality of the silymarin cyclodextrin inclusion compound prepared by the patent application, which may influence the safety and effectiveness of silybin.

③ Complete Re-dissolution can't be Realized

The freeze-dried sample is re-dissolved with water for injection, sodium chloride injection of 0.9% and glucose injection of 5% respectively. The results indicate that all the re-dissolution solutions show obvious turbidity, and that turbidity becomes serious after the solutions are placed aside, with precipitates appearing. However, the re-dissolution property of the silybin injection of the present invention after freeze-drying is good. Therefore, there are obvious differences.

In conclusion, for Chinese patent application CN02125823.6 with the title "silymarin injection containing cyclodextrin or derivatives thereof" and the publication number of CN1391894A, the implementing scheme recorded in the Description has poor feasibility, and the selected variety of cyclodextrin is not the best matching for silybin (see embodiment 1 of the present invention). Therefore, the safe and stable silybin injection can't be obtained.

The invention claimed is:

1. A composition, comprising silybin, sulfobutylether-β-cyclodextrin, an organic solvent for injection, and a pH regulator, wherein the pH regulator is not NaOH and HCl.

2. The composition of claim 1, further comprising a cosolvent selected from one or more of distearoyl phosphatidylethanolamine-polyethylene glycol 2000, distearoyl phosphatidylethanolamine-polyethylene glycol 5000, polysorbate 80, polyoxyl hydrogenated castor oil, and poly(ethylene glycol)-block-poly(propylene glycol)-block-poly(ethylene glycol).

3. The composition of claim 1, comprising the following components by weight/volume percentage:

| | |
|---|---|
| silybin | 0.05-1.0% |
| sulfobutylether-β-cyclodextrin | 2-50% |
| organic solvent for injection | 0.5-10% |
| cosolvent | 0-1.0% |
| bulking agent | 0-20% |
| pH regulator | regulating the pH value to be 2.0-8.0 |
| water for injection | the balance. |

4. The composition of claim 3, comprising the following components by weight/volume percentage:

| | |
|---|---|
| Silybin | 0.1-0.8% |
| sulfobutylether-β-cyclodextrin | 2-30% |
| organic solvent for injection | 0.5-5% |
| cosolvent | 0.001-0.5% |
| bulking agent | 0-15% |
| pH regulator | regulating the pH value to be 2.0-7.0 |
| water for injection | the balance. |

5. The composition of claim 4, comprising the following components by weight/volume percentage:

| | |
|---|---|
| Silybin | 0.1-0.5% |
| sulfobutylether-β-cyclodextrin | 2-10% |
| organic solvent for injection | 1-5% |
| cosolvent | 0.005-0.5% |
| bulking agent | 3-10% |
| pH regulator | regulating the pH value to be 2.5-6.0 |
| water for injection | the balance. |

6. The composition of claim 1, wherein the organic solvent for injection is selected from one or more of polyethylene glycol 200, polyethylene glycol 300, polyethylene glycol 400, polyethylene glycol 600, and propylene glycol.

7. The composition of claim 3, wherein the bulking agent is selected from one or more of mannitol, lactose, dextran 20, dextran 40, dextran 70, sucrose, xylitol, sorbitol and trehalose.

8. The composition of claim 1, wherein the pH regulator is selected from one or more of citric acid, hydrochloric acid, glacial acetic acid, phosphoric acid, disodium hydrogen phosphate, sodium dihydrogen phosphate, dipotassium hydrogen phosphate, monopotassium phosphate, disodium citrate, trisodium citrate and sodium acetate, wherein the pH regulator regulates at pH 2 to 8.

9. The composition of claim 1, in the form of a silybin solution suitable for injection.

10. A method of preparing the composition of claim 9 comprising: mixing silybin and the organic solvent for injection, and heating and stirring the mixture at 40° C. to 70° C. to obtain an organic phase; mixing the sulfobutylether-β-cyclodextrin and water to obtain an aqueous phase; mixing the organic phase with the aqueous phase to obtain a medicine solution; adding the pH regulator to regulate the pH value of the medicine solution to be pH 2 to 8; treating the medicine solution with 0.05 w/v %-0.5 w/v % activated carbon, filtering the solution through a 1 μm titanium rod, and then through a 0.22 μm filter.

11. The composition of claim 1, in the form of freeze-dried preparation for injection, wherein the organic solvent for injection is selected from polyethylene glycol or propylene glycol.

12. A method of preparing the composition of claim 11 comprising: mixing silybin and the organic solvent for injection, and heating and stirring the mixture at 40° C. to 70° C. to obtain an organic phase; mixing sulfobutylether-β-cyclodextrin, a bulking agent, and to obtain an aqueous phase; mixing the organic phase with the aqueous phase to obtain a medicine solution; adding a pH regulator to regulate the pH value of the medicine solution to be pH 2 to 8; treating the medicine solution with 0.05 w/v %-0.5 w/v % activated carbon filtering the solution through a 1 μm titanium rod, filtering through a 0.22 μm filter; and performing sub-packaging, freeze-drying and sealing.

13. The composition of claim 6, wherein the organic solvent for injection is polyethylene glycol 400.

14. The composition of claim 2, wherein the cosolvent is distearoyl phosphatidylethanolamine-polyethylene glycol 2000.

15. The composition of claim 7, wherein the bulking agent is mannitol, lactose, or dextran 40.

16. The composition of claim 8, wherein the pH regulator regulates at pH 2.0 to 7.0.

17. The composition of claim 16, wherein the pH regulator regulates at pH 2.5 to 6.0.

18. The method of claim 10, further comprising a step of adding a cosolvent to the organic phase, wherein the cosolvent is selected from one or more of distearoyl phosphatidylethanolamine-polyethylene glycol 2000, distearoyl phosphatidylethanolamine-polyethylene glycol 5000, polysorbate 80, polyoxyl hydrogenated castor oil, and poly(ethylene glycol)-block-poly(propylene glycol)-block-poly(ethylene glycol).

19. The method of claim 12, further comprising a step of adding a cosolvent to the organic phase, wherein the cosolvent is selected from one or more of distearoyl phosphatidylethanolamine-polyethylene glycol 2000, distearoyl phosphatidylethanolamine-polyethylene glycol 5000, polysorbate 80, polyoxyl hydrogenated castor oil, and poly(ethylene glycol)-block-poly(propylene glycol)-block-poly(ethylene glycol).

* * * * *